United States Patent [19]

Ledbetter

[11] Patent Number: 5,782,875
[45] Date of Patent: Jul. 21, 1998

[54] METHOD OF PREVENTING OSTEOPOROSIS

[75] Inventor: John C. Ledbetter, Billings, Mont.

[73] Assignee: The Nyvatex Marketing Corporation, Billings, Mont.

[21] Appl. No.: 904,820

[22] Filed: Aug. 1, 1997

Related U.S. Application Data

[63] Continuation of Ser. No. 484,295, Jun. 7, 1995, abandoned.

[51] Int. Cl.$^6$ ............................................. A61N 1/00
[52] U.S. Cl. ....................................... 607/2; 607/51
[58] Field of Search ........................... 607/2, 50, 51; 600/9, 13–15

[56] References Cited

U.S. PATENT DOCUMENTS

| | | | |
|---|---|---|---|
| 499,681 | 6/1893 | Renstrom | 600/13 |
| 3,848,588 | 11/1974 | Miquel | 600/13 |
| 4,330,892 | 5/1982 | Fukushima | 600/13 |
| 4,587,956 | 5/1986 | Griffin et al. | 600/15 |
| 4,793,325 | 12/1988 | Cadossi et al. | 607/51 |
| 5,160,591 | 11/1992 | Liboff et al. | 600/15 |
| 5,226,185 | 7/1993 | Guay et al. | 600/15 |
| 5,267,939 | 12/1993 | Liboff et al. | 600/15 |
| 5,413,596 | 5/1995 | Kronberg | 607/51 |
| 5,453,074 | 9/1995 | Iomoto | 600/15 |
| 5,607,453 | 3/1997 | Ishiguro et al. | 607/2 |

FOREIGN PATENT DOCUMENTS

| | | | |
|---|---|---|---|
| 2688697 | 9/1993 | France | 600/13 |
| 3904304 | 8/1990 | Germany | 607/51 |
| 766607 | 9/1980 | U.S.S.R. | 607/51 |

OTHER PUBLICATIONS

Gutterman, Steve. Part II: Brighton Beach Maladies. Newsday, Dec. 2, 1993, p. 68.
Kramer, Mark. Part II: Related by Blood. Newsday, Sep. 22, 1994, p. 4.
Wright, Lili. Latinos Rich Heritage of Church. The Salt Lake Tribune, Apr. 3, 1994, p. A13.
Valentine, Tom. The National Exchange, vol. 3, No. 6, Mar. 1979.
Kolata, Gina. Study Says 1 in 5 Americans . . . . The New York Times, Oct. 21, 1994.
300–plus Alternative Medicines Exist, Memphis Commercial Appeal, Feb. 26, 1995, p. E3.

*Primary Examiner*—William E. Kamm
*Assistant Examiner*—Kennedy J. Schaetzle
*Attorney, Agent, or Firm*—Darby & Darby

[57] ABSTRACT

Disclosed herein is a method for preventing osteoporosis in a human patient by contacting the patient with an electromagnetic (EM) capture and generator device for a time effective for preventing the disease.

3 Claims, 1 Drawing Sheet

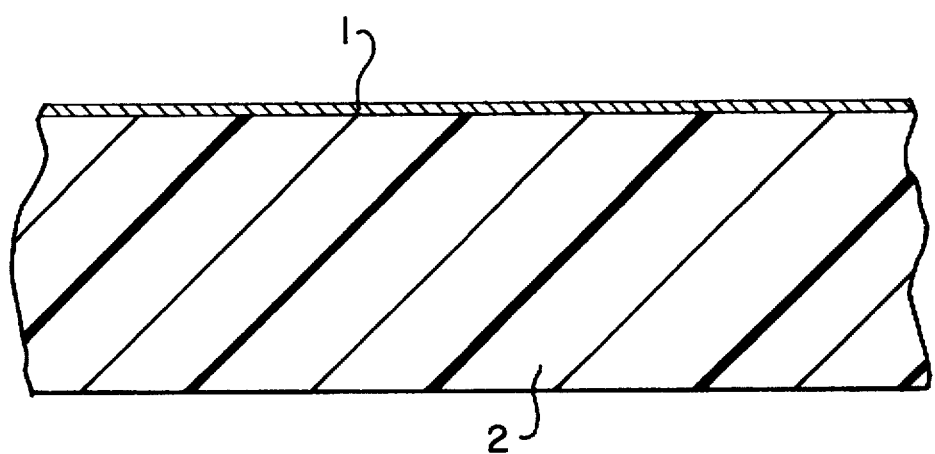

METHOD OF PREVENTING OSTEOPOROSIS

This is a continuation, of application Ser. No. 08/484, 295, filed Jun. 7, 1995, now abandoned.

FIELD OF THE INVENTION

The present invention is directed to methods of preventing the symptoms of osteoporosis in mammals.

BACKGROUND OF THE INVENTION

Osteoporosis is the term used for a group of diseases of diverse etiology characterized by a reduction in the mass of bone to a level below that required for adequate mechanical support function. After the age of 40–50, skeletal mass begins to decline at a faster rate in women than in men and is particularly apparent in post-menopausal women. Osteoporosis is the commonest of the metabolic bone diseases and an important cause of morbidity in elderly patients.

Estrogens produce significant, although modest, calcium retention, decrease the difference between formation and resorption of bone, and therefore tend to retard the progress of osteoporosis. However, the use of estrogens is limited due to the known dose-related increase in the incidence of endometrial carcinoma with their use.

Oral calcium is also used to prevent osteoporosis. Intermittent intravenous infusions of calcium have also been advocated, but the efficacy has yet to be established.

Therefore, what is needed in the art are methods for preventing osteoporosis which are effective, do not require hormonal or other vitamin supplemental therapy, and have little or no side effects. The present invention provides such a method.

BRIEF DESCRIPTION OF THE DRAWINGS

FIG. 1 is a schematic representation of one layer of the EM capture and generator device of the present invention.

The present invention is based on the inventor's "Field Effect Theory of Wellness". It was realized that all living things are in a "sea"or "a bath" of non-linear electromagnetic (hereinafter EM) radiation that was just at the correct intensity to maximize an energy component of cellular development. As the human body had evolved over millions of years in this "EM bath", the body continued to achieve its best potential in this "bath of energy". As humans advanced to high-rise apartments, paved cities, etc., they were well-clothed, wearing well-soled shoes, riding in cars, trains, planes, etc., and they were not getting the proper non-linear EM energy input. This has led to a variety of maladies with seemingly no "cause".

The present inventor realized that the human body was a capacitor and a conductor of EM energy that can store enough charge at a high enough voltage to provide sparking. This is seen when walking across a carpet on a low humidity day and having sparks jump between a finger and some metal object, such as a door knob. The capacitance of the average human is approximately 100 picofarads. These energies reflect interaction with the Earth. In addition, the present inventor discovered an appropriate flux density of this EM energy. The flux density is energy per unit time (power) passing through a unit of surface.

All human bodies contain several trillion cells, and it is generally accepted that good cell communication is an essential part of good health. A cell has about 25,000 different types of molecules floating around in it. A cell is a system for processing information via its bioelectrochemical networks. The molecular manipulations are dictated by chemical messages both intrinsic and extrinsic to the cell. These chemical messages and their transport are further dictated by electric field potentials.

The cell is surrounded by an outside membrane and spaces inside the cells are divided by many membranes into highly complicated structures known as organelles. Internal and external cellular communication across these membranes control all life functions. Calcium (CA++) ion exchange between cells is a prime example of this absolutely essential communication.

The fluid in a living human cell is rich in potassium chloride, while the fluid outside contains sodium chloride. The outer membrane of a resting cell is far more permeable to ionic potassium than sodium, so that positive ions depart the interior of the cell which leaves the interior of the cell with a negative charge. This is generally referred to as the sodium-potassium "pump". This results in a voltage across the membrane of about −90 MV (Ninety Millivolts), referred to as the resting potential. The membrane is about 50 atom layers thick (about 8 Billionths of a meter) resulting in an electric field strength of about 10 thousand volts per meter in magnitude. Cell communication, nerve pulses, thinking, etc., require electric field action potentials to set up and propagate the bioelectrochemical pulse trains that control all life functions.

Thus, it can be seen that manipulating the EM energy can have profound effects on humans, if a device were available to perform this function.

One object of the present invention is to localize, collect, amplify and reproduce the non-linear elements of the earth's EM field and space radiation that provide electric action potentials for all life processes, both fauna and flora.

A further object is to provide an artifact, tool, or machine that passively energizes so that no apparent power source is required.

A still further object of the present invention to is use the device to prevent the symptoms of osteoporosis.

DETAILED DESCRIPTION OF THE INVENTION

The present invention provides a device (described further below) to store EM energy and generate this energy to a subject in contact with it. The device will alternatively be referred to as an "EM capture and generator."

The aspect of the electric field that is somewhat static and slowly time varying, coupled with the electromagnetic (linear and non-linear) universal bombardment from space radiation of four gigahertz to twelve gigahertz (inclusive) is to be captured, stored and resonate about the device.

A schematic representation of one layer of the EM capture and generator device of the present invention is shown in FIG. 1. In FIG. 1 a vapor deposited metal conductor (aluminum) about 200 Angstron thick is in contact with (2) a dielectric polyester, 48 gauge thick (.00048 inches). This is then stacked in 25 to 200 layers, conductor to dielectric.

The effect becomes most pronounced at about 25 layers, and seems to maximize at 100 layers. The multiple layers are fully covered with a long-lasting, non-conducting material and stitched together for durability and longevity. The thread is of any non-conducting material.

This is a metal coated polyester film. Vapor deposition is a well known process used in the manufacture of many items, such as aluminized mylar, etc. A specification of about 250 Angstroms on 48 gauge (.00048 inch) polyester gave the necessary relationships. Stacking of 100 layers, coated side to uncoated side, provided the mechanical arrangement that made for the proper non-linear electromagnetic properties. Capacitors for electric circuits are made in this fashion, and are known as parallel plate capacitors. Area is important. Too small an area cannot achieve the non-linear EM effect. 15"×24" or 8"×36" seem to be the lower limits for best results.

This arrangement provided the preferred cross section capture area of these naturally occurring non-linear EM earth fields. These naturally occurring fields are quite faint, on the order of 100 volts per meter. The device concentrates the field at about 500 volts per meter. The amperage is negligible.

Once the energy is concentrated in the device, it can be used as a generator. Contact electrification is known by the term triboelectrification, or friction-induced electrification. Different materials have different affinities for electrons. When differing substances are put into contact, one will give up electrons and the other will gain electrons. Electron movement between contact materials is dependent upon their ranking in the triboelectric sequence. In the device, the 100 layers of polyester film rub against the 100 layers of metal causing electron transfer and an electric charge to be induced. The combination of all these events creates a non-linear EM field of the desired type, i.e., similar to the natural field surrounding the earth. This created non-linear EM field added to the collected field greatly increases the available EM field for the human body adjacent to the device.

The weight of the human body on the device does increase the friction between the 100 alternating layers, and via the phenomena of triboelectrification increases electron transfer thereby increasing the charge, and generating a more intense non-linear EM field. The weight of the human body thereby in reality becomes a motive force to generate the desired EM field. The farther apart the materials are in the triboelectric sequence, the more intense the resulting electrification. Polyester and aluminum are far enough apart in the series for this use.

With the above described design, a further non-linear EM field generator is achieved. This occurs due to intermolecular forces of attraction due to fluctuating dipole moments. In a solid body, these forces are variously called London, van der Waals, or dispersion forces.

By separating the solid body conductor, (a metal-aluminum) from another like layer, etc. etc., using a very thin polyester (a polymeric molecule film) molecular dipole attractions are created between the separated conducting substance (aluminum); this attraction creates a polarized field providing the non-linear EM twist to the entire device. This exactly duplicates at higher flux densities the natural earth field.

These permanent electrostatic and time-varying interactions modulate the generated field. Collection, generation and amplification of the natural earth non-linear EM field, to a few hundred times that normally existing, gives the desired result.

This boosted EM field is "seen" by the body's cells and all cellular transactions are thereby enhanced. The stronger the field, the more movement (energy) is imparted to a charged particle (such as an ion) in that field. Sluggish ion transport is then speeded up, the immune system is re-energized, and all systems proceed into harmonious, fast acting, first order functioning. Prior problems get resolved and future problems are denied.

Such a device is commercially available as the NYVATEX HARMONY BLANKET™ (The Nyvatex Marketing Corporation, Billings, Mont.). It is available in three models (Model 50, Model 50A and Model 100). They are approximately 24"×42" with the strongest being the Model 100. The Model 100 is preferred for use in the present invention.

In accordance with the present invention, a patient at risk for developing osteoporosis contacts the device of the present invention for a time effective to prevent osteoporosis. The effective time is preferably between about 1 and 2 hours, twice per day, and most preferably sleeping on it overnight. The device is preferably used every day. The major portion of patient's body should contact the device. In addition, the patient's body should not be separated from the device by more than one thickness of clothing.

The device aids human body calcium transport and uptake into the mass of the skeleton, and therefore is effective in avoiding the development of osteoporosis. As shown below in Example 1, baseline data has been obtained from a patient at risk for developing osteoporosis. The patient will be monitored at regular intervals to check her progress.

The present invention is described further below in specific examples which are intended to further describe the invention without limiting its scope.

EXAMPLE 1

A 49 year old, post-menopausal, light skinned, blonde woman underwent a CT scan for osteoporosis. The T11, T12, L1 and L2 vertebral bodies were individually scanned with a 10mm thickness slice and comparison made at each level by a commercial Imaging company (Portland Imaging, Rochester, N.Y.). The following bone mineral values were obtained:

|        | T11 | T12 | L1  | L2 |
|--------|-----|-----|-----|----|
| mg/cm$^3$ | 125 | 111 | 119 | 95 |

Average bone density was 112.5 mg/cm$^3$.

The values for T11, T12, and L1 were within one standard deviation of the mean for the patient's age, the value for L2 vertebral body was greater than one standard deviation below the mean for the patient's age.

The patient slept on a Model 100 Harmony Blanket™ every night and did not consistently take any other treatment (e.g., increased dietary calcium, estrogen, etc.).

Four months later, a follow-up scan was performed. The results are set forth below.

|        | T11 | T12 | L1  | L2  |
|--------|-----|-----|-----|-----|
| mg/cm$^3$ | 93  | 115 | 111 | 114 |

Compared with the prior study, the values are similar within a 10% margin for error.

What is claimed is:

1. A method for preventing osteoporosis in a human patient comprising contacting a patient in need of such treatment with an EM capture and generator device for a time effective for preventing osteoporosis.

2. The method of claim 1 wherein said effective time is between about one and about two hours twice a day.

3. The method of claim 1 wherein said effective time is overnight.

* * * * *